United States Patent [19]

Otake et al.

[11] Patent Number: 4,521,339

[45] Date of Patent: Jun. 4, 1985

[54] ANSATRIENOLS

[75] Inventors: Noboru Otake, Yokohama; Haruo Seto, Hachioji; Tetsuo Sasaki, Kounosu; Masanori Sugita, Sakado; Yohei Natori, Tokyo; Noriyoshi Sueda, Kawagoe, all of Japan

[73] Assignee: Nisshin Flour Milling Co., Ltd., Japan

[21] Appl. No.: 444,474

[22] Filed: Nov. 24, 1982

[30] Foreign Application Priority Data

Nov. 27, 1981 [JP] Japan ............................ 56-189237
Nov. 27, 1981 [JP] Japan ............................ 56-189238
Dec. 18, 1981 [JP] Japan ............................ 56-203558

[51] Int. Cl.$^3$ ..................... C07D 225/06; C12P 17/10
[52] U.S. Cl. ............................ 260/239.3 B; 435/121
[58] Field of Search ................................ 260/239.3 B

[56] References Cited

FOREIGN PATENT DOCUMENTS 45-17598  6/1970  Japan .......................... 260/239.3 B

OTHER PUBLICATIONS

Damberg et al., "Tetrahedron Letters", vol. 23, No. 1, pp. 59–62, (1982).
Chemical Abstracts, vol. 98, (1983), Item 103963u abstracting Sugita et al. in "J. Antibiotics", (1982), vol. 35, No. 11, pp. 1474–1479.
Coronelli et al., "The Journal of Antibiotics", Series A, vol. XX, No. 6, (1967), pp. 329–333.

*Primary Examiner*—Robert T. Bond
*Attorney, Agent, or Firm*—Abelman Frayne Rezac & Schwab

[57] ABSTRACT

The disclosure describes a microbiological process for the preparation of mycotrien-related compounds.

The compounds are isolated and characterized by structural formula and other identifying data.

The compounds are useful in the treatment of tumors.

4 Claims, 4 Drawing Figures

PMR of T-23-IV

ANSATRIENOLS

This invention relates to mycotrienin-related compounds having novel chemical structures.

During the course of screening anti-tumor substances, it has now been found that a certain new microorganism belonging to *Streptomyces rishiriensis*, which is called hereafter "*Streptomyces rishiriensis* T-23" strain, can produce two metabolites interconvertible to each other, said metabolites being effective to inhibit the growth of L-5178Y lymphoma cells. We designated these metabolites as being a T-23-I substance and a T-23-II substance. As the result of our investigation, we could have ascertained their chemical structures, and we have further found that these T-23-I and -II substances can be converted into their two analogues, T-23-III and T-23-IV substances.

The following scheme illustrates the mutual relation of the T-23-I, T-23-II, T-23-III and T-23-IV substances in chemical conversion:

The dashed line means a biological route whereas the solid lines do chemical routes. The structural formulae of the T-23-I, -II, -III and -IV substances will be indicated hereinafter.

T-23-I and -II substances can be obtained by cultivation of a new strain *Streptomyces rishiriensis* T-23, which was deposited at "Fermentation Research Institute, Agency of Industrial Science & Technology, MIT (Japan)" under the deposit number FERM P-6141. Mycological and other characteristics of the strain are given below:

(a) Morphological properties:

The vegetative mycelium of the strain T-23 develops well without fragmentation on most of the media used. The aerial mycelium monopodially branches with short sporophores forming spore chains with 10 to 50 or sometimes more than 50 spores per chain. The spore chains are usually loose coils (Spira), and chains with terminal hooks or loops and primitive spirals (*Rectus flexibilis*) are also common (Plate 1). The spores are oval to cylindrical ($1.0-1.5 \times 0.5-0.7$ m$\mu$) with a smooth surface under the electron microscope (Plate 2). Sporangia, motile spores, sclerotia and other special morphology are not observed.

(b) Cultural properties:

The cultural properties of strain T-23 grown on various media at 27° C. for 2 to 3 weeks are indicated below. The observation was done in the methods as described in "Methods Manual 1941", edited by International Streptomyces Projects.

| Media | Growth | Sporulation | Color of colony | Reverse side of colony | Color in media |
|---|---|---|---|---|---|
| Sucrose-nitrate agar (Waks, No. 1) | moderate | poor | white | pale yellow | none |
| Glucose-asparagine agar (Waks, No. 5) | moderate | moderate | Gray color series (brownish gray to reddish gray) | brownish white to light yellow | none |
| Glycerol-asparagine agar (ISP No. 5) | poor | poor | white to light gray | brownish whith to pale yellow | none |
| Inorganic salt-starch agar (ISP No. 4) | moderate | moderate | Gray color-series (reddish gray to purplish gray) | light gray | none |
| Tyrosine agar (ISP No. 7) | poor | poor | white to grayish white | brownish white to pale yellow | light brownish gray |
| Nutrient agar (Waks, No. 14) | poor | none | white | brownish white or pale yellow to pale yellowish brown | pale yellowish brown |
| Yeast extract-malt extract agar (ISP No. 2) | moderate | moderate | Gray color-series (reddish gray to dark purplish gray) | pale yellow orange to pale yellowish brown | pale yellowish orange |
| Oatmeal agar (ISP No. 3) | moderate | moderate | Gray color-series (reddish gray to purplish gray) | pale yellow to pale yellowish brown | none or trace of of brownish |

(c) Physiological properties:
Temperature for growth: 10°–37° C.
Temperature for optimum growth: 20°–30° C.
Liquefaction of gelatin: + (positive)
Hydrolysis of starch: +
Coagulation of non-fat milk: − (negative)
Peptonization of non-fat milk: +
Formation of melanoid pigments: +
Tyrosine agar: +
Peptone-yeast extract agar: +
Tryptone-yeast extract broth: +

(d) Utilization of carbon sources (Pridham-Gottlieb's agar medium):
L-Arabinose: + + (Well growth)
D-Xylose: + +
D-Glucose: + +
D-Fructose: + (Poor growth)
Sucrose: + +
Inositol: + +
L-Rhamnose: + +
Raffinose: + +

D-Mannitol: — (No growth)

These properties of the strain could be summarized as follows: aerial mass color is Gray color-series, brownish gray or reddish gray to dark purplish gray; reverse side of colony shows no distinctive pigments, brownish white to light yellow on synthetic media and pale yellowish brown on organic media; melanoid pigments are formed on the ISP's test media, and other soluble pigments are not found in most media; the strain is mesophilic, and possesses diastatic and proteolytic natures; and all tested sugars except D-mannitol are utilized for growth as carbon sources.

On the consideration of its features, the T-23 strain is recognized as belonging to the genus Streptomyces. Among the species of Streptomyces described in the 8th edition of Bergey's manual, the T-23 strain closely resembles S. rishiriensis. The properties of the strain are compared with those of S. rishiriensis, and good agreements are obtained except soluble pigments on organic agar media. Therefore, the T-23 strain is identified as a strain of S. rishiriensis.

For the production of the T-23-I and -II substances, the fermentation of the above-mentioned Streptomyces T-23 strain is conducted according to the method for the fermentation of any Actinomyces strain. As a carbon source, saccharides such as glucose, lactose and fructose, starch, and starch hydrolyzates are usable alone or in combination. The mixture of starch and glucose is preferable. As a nitrogen source, meat extract, polypeptone, soya flour, corn steep liquid and several inorganic nitrogen sources are usable. To facilitate the fermentative production, some additives, i.e., dry yeast, maltose extract and other several plant seed extracts, vitamines, and several inorganic salts may be added. If necessary, an antifoam agent such as silicone oil, vegetable oil, etc., can be added. The culture of strain can be carried out by using a flask, jar fermenter or larger scale fermentation tank. The temperature for cultivation is 20° to 35° C. and preferably 25° to 30° C., and a submerged culture system is employed. The time for cultivation is 17 to 96 hours and the peak of production of the T-23-I and -II substances is attained at around 24 hours after the initiation of the cultivation.

The T-23-I and -II substances are insoluble in water and soluble in higher alcohols, acetone, chloroform, benzene and ethylacetate, and therefore, a suitable purification method is to be selected depending upon such solubility features.

An example is shown below to illustrate the recovery of the T-23-I and -II substances.

The T-23-I and -II substances are mainly accumulated in the mycelia, while some also is present in a supernatant. After the cultivation, the culture broth was cooled soon and then divided into mycelia and a supernatant by centifuge or filtration. The mycelia were treated with 60–70% aqueous acetone. The extract which contained the active fraction was filtered. The filtrate was passed through a non-ionic exchange resin to effect the absorption of the active fraction thereon, and then the active portion was eluted with an organic solvent such as a lower alcohol or acetone or an aqueous solution containing such organic solvent. Alternatively, it is also possible to extract the active portion with an organic solvent directly from the filtrate.

The active portion similarly obtained from the supernatant was combined with an extract of mycelia. The mixture obtained was adjusted to a pH of 5.0–6.0, and the organic solvent which exsisted was evaporated off under reduced pressure. The active substance was extracted from the aqueous phase with a water-immiscible solvent such as chloroform, ethyl acetate or isopropyl alcohol in the absence or presence of an industrially usable inorganic salt such as sodium chloride in order to improve the efficiency of extraction. The extract obtained was added with anhydrous sodium, sulfate, allowed to stand for a while to effect dehydration and then concentrated under reduced pressure. Then, the residue obtained was added with petroleum ether or hexane thereby to effect the precipitation of a physiologically active product which was found to consist of the T-23-I and -II substances. These substances were further separated by chromatographic operation using silicic acid, non-ionic exchange resin, cephadex LH-20, etc. The following is an example of the method for preparation of highly purified T-23-I and/or T-23-II substances by way of liquid chromatography.

Silicic acid was filled, with the aid of benzene, into a column to which a sample containing both of the T-23-I and -II substances were then charged. The fraction eluted first by passing benzene through the column was discarded. Then, the T-23-I substance was eluted with a mixed solvent consisting of benzene-acetone (4:1). The active fractions obtained were concentrated under reduced pressure, and a non-polar solvent such as petroleum ether or hexane was added to have the T-23-I substance crystallized. The T-23-I substance thus obtained can be subjected, if needed to further purification by chromatography or recrystallization to yield the highly purified T-23-I substance. The T-23-II substance was eluted by passing a mixed solvent of benzene/acetone (7:3) through said column. The highly purified T-23-II substance was obtained in the same manner as for the T-23-I substance.

Further, it is to be noted that the T-23-I and -II substances are chemically interconvertible each other. By reduction with $Na_2S_2O_4$, for example, the T-23-I substance can be readily converted to the T-23-II substance, and the reverse reaction can be accomplished by oxidation with air or $FeCl_3$.

The physicochemical properties of the T-23-I and -II substances are set forth below.

T-23-I substance (1) Appearance: Amorphous, yellow powder
(2) Structural formula:

(3) $[\alpha]_D^{25} = +91.8$ (CHCl$_3$, C = 1.0%)
(4) m.p. 117° C. (decomp.)
(5) Elementary analysis as $C_{36}H_{48}N_2O_8$:

|  | C % | H % | N % | O % |
| --- | --- | --- | --- | --- |
| Calculated: | 67.92 | 7.55 | 4.40 | 20.13 |
| Found: | 67.72 | 7.68 | 4.28 | 19.74 |

(6) UV absorption

| λ max | Molar extinction |
| --- | --- |
| 262 nm | $\epsilon = 38500$ |
| 272 nm | $\epsilon = 49600$ |
| 282 nm | $\epsilon = 38800$ |
| 383 nm | $\epsilon = 3400$ |

-continued

Figure 1:
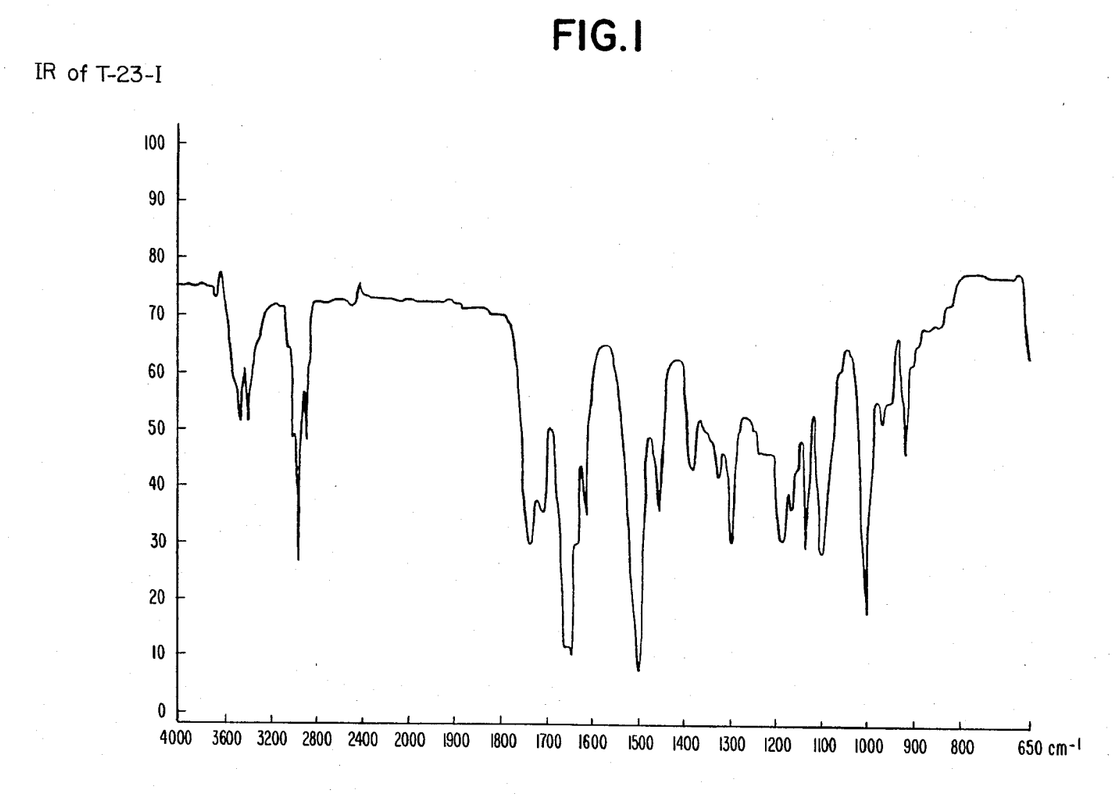

| | | |
|---|---|---|
| (7) | IR absorption (See FIG. 1) | |
| | 3330 cm$^{-1}$  1460 cm$^{-1}$  1100 cm$^{-1}$ | |
| | 1730 cm$^{-1}$  1376 cm$^{-1}$  998 cm$^{-1}$ | |
| | 1650 cm$^{-1}$  1300 cm$^{-1}$  849 cm$^{-1}$ | |
| | 1535 cm$^{-1}$  1202 cm$^{-1}$  720 cm$^{-1}$ | |
| (8) | $^{13}$C—NMR (in CDCl$_3$) | |

| Group | Shift |
|---|---|
| —C(=O)— | 188.2, 182.5 |
| —C(=O)—NH— | 176.6, 169.4 |
| —C(=O)—O— | 172.9 |
| \C= / | 145.4, 137.9, 129.3 |
| \CH= / | 139.9, 133.7, 133.6, 133.2, 133.1, 131.3, 129.5, 122.5, 114.5 |
| \CH—O / | 79.2, 75.2, 68.0 |
| —OCH$_3$ | 56.6 |
| —C(=O)—CH(—)—NH— | 48.5 |
| —C(=O)—CH(—)— | 44.9 |
| —C(=O)—CH$_2$— | 44.8 |
| \CH— / | 39.9 |
| —CH$_2$— | 33.0, 29.4, 29.4, 29.3, 25.6, 25.6, 255.5, 25.5 |
| —CH$_3$ | 20.5, 17.4, 9.6 |

(9) PMR (in CDCl$_3$)

| Group | Signal |
|---|---|
| \CH—CH$_3$ / | 0.90 3H, d<br>1.41 3H, d |
| =C(CH$_3$)/ | 1.80 3H, s |
| —OCH$_3$ | 3.28 3H, s |
| —OCH< | 4.02 1H, dt<br>4.75 1H, bs |
| —NH—CH(CH$_3$)— | 4.96 1H, dd<br>4.36 1H, dq |
| Aromatic H | 6.50 1H, d<br>7.51 1H, d |
| CONH | 8.18 1H, s |

-continued

| | | |
|---|---|---|
| (10) | Color reaction: | |
| | Ninhydrin | (−) |
| | Biuret | (−) |
| | Anthrone | (−) |
| | Fehling | (+) |
| (11) | Solubility in solvents:<br>Soluble in methanol, ethanol, acetone, chloroform and ethyl acetate,<br>Sparingly soluble in benzene and ether,<br>Insoluble in water, petroleum ether and hexane | |
| (12) | Cyclohexylalanine as the 11-positioned ester-forming component is in D-form. | |

T-23-II substance (1) Appearance: Amorphous, white powder
(2) Structural formula (3) $[\alpha]_D^{25} = +288°$ (c = 1.0% in CH$_3$OH)
(4) m.p. 151° C. (decomp.)
(5) Elementary analysis as C$_{36}$H$_{50}$N$_2$O$_8$:

| | C % | H % | N % | O % |
|---|---|---|---|---|
| Calculated: | 67.72 | 7.68 | 4.28 | 20.32 |
| Found: | 67.92 | 7.55 | 4.40 | 20.13 |

(6) UV absorption

| λ max | Molar extinct. |
|---|---|
| 260 nm | ε = 40800 |
| 270 nm | ε = 52300 |
| 280 nm | ε = 40500 |
| 310 nm | ε = 5900 |

Figure 2:
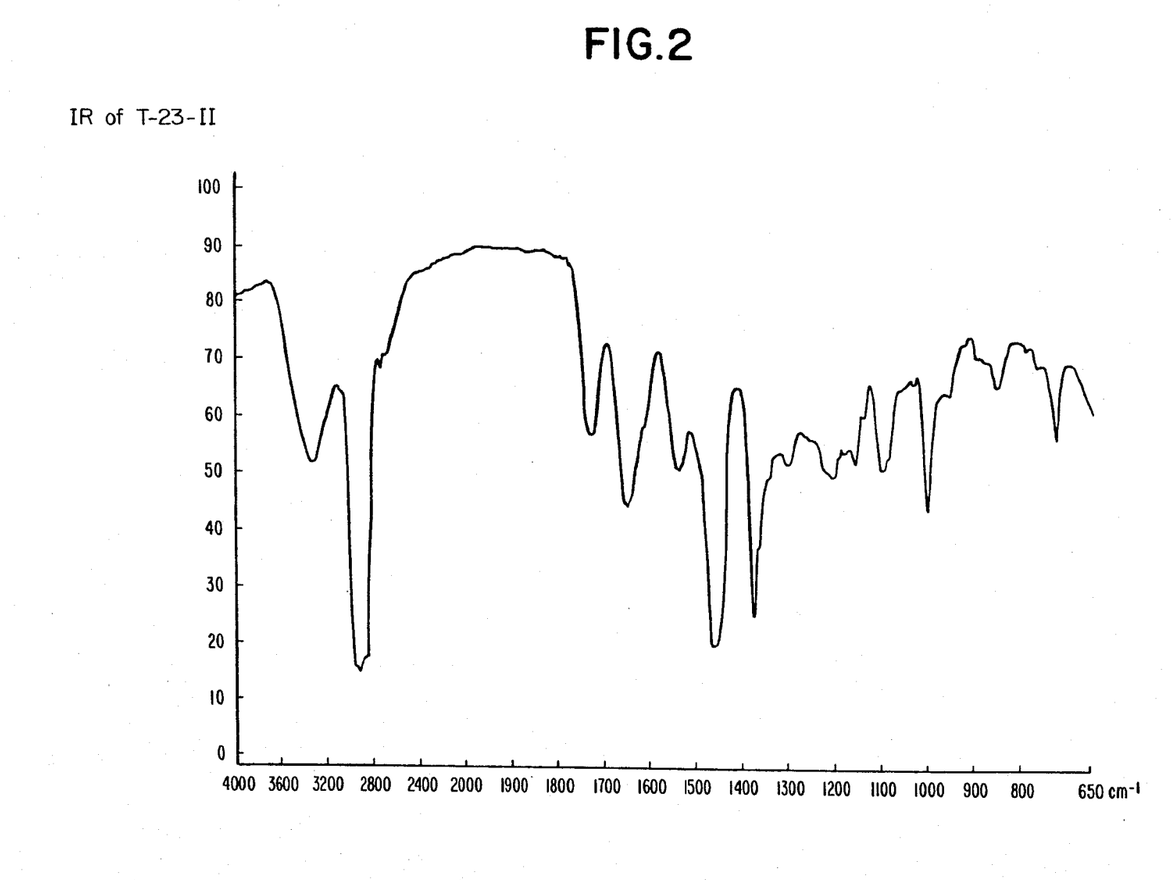

(7) IR absorption (See FIG. 2)
3340 (NH, OH), 1730, 1200 (ester),
1650, 1535 (amide)
(8) $^{13}$C—NMR (in CDCl$_3$)

| Group | Shift |
|---|---|
| —HN—C(=O)— | 176.9, 173.3 |
| —O—C(=O)— | 179.7 |
| \C= / | 149.2, 141.1, 137.8, 132.7, 125.5 |
| \CH= / | 134.9, 134.4, 133.9, 129.6, 129.5, 129.1, 124.3, 115.8, 107.5 |
| \CH—O— / | 79.6, 75.8, 68.7 |
| —O—CH$_3$ | 56.6 |
| —C(=O)—CH(—)—NH— | 48.7 |
| —C(=O)—CH(—)— | 45.1 |

| | |
|---|---|
|  —C—CH$_2$— | 43.1 |
|  ⟩CH— | 39.0 |
| —CH$_2$— | 33.7, 31.7, 29.5, 29.4, 26.7 26.6, 25.7, 25.6 |
| —CH$_3$ | 20.3, 17.7, 9.7 |

(9) PMR (in d-pyridine)

| | |
|---|---|
|  ⟩CH—CH$_3$ | 0.85 3H, d 1.57 3H, d |
|  =⟨CH$_3$ | 1.98 3H, s |
| —OCH$_3$ | 3.27 3H, s |
|  —O—CH⟨ | 4.49 1H, dt 5.28 1H, bs |
|  —NH—CH—\|CH$_3$ | 5.36 1H, dd 4.80 2H, dq |
|  =⟨H | 5.53 1H, m 5.70 1H, dd 6.06 1H, m 6.23 1H, dd 6.37 1H, dd 6.53 1H, dd 6.64 1H, dd |
| Aromatic H | 7.12 2H, s |
| CONH | 8.78 1H, bs 9.01 1H, d |

(10) Color reaction:
    Ninhydrin   (−)
    Biuret   (−)
    Anthrone   (−)
    Fehling   (+)

(11) Solubility in solvents:
Soluble in chloroform, methanol, ethanol, acetone and ethyl acetate,
Sparingly soluble in benzene and ether,
Insoluble in water, petroleum ether and hexane.

(12) Cyclohexylalanine as the 11-positioned ester-forming component is in D-form.

T-23-III and -IV substances can be obtained by removing the side chain including a cyclohexane ring on the 11-positioned carbon atom by reduction. Such reduction can be carried out by catalytic hydrogenation using lithium aluminum hydride or platinum carbon in the conventional manner.

The physicochemical properties of the T-23-III and -IV substances thus obtained are summarized below:

(1) Appearance: Yellowish orange-colored amorphous powder
(2) Structure formula (MW 455)

(3) $[\alpha]_D^{25} = +4.3°$ (c = 1% in MeOH)
(4) m.p. 94–95° C.
(5) Elementary analysis as C$_{36}$H$_{33}$NO$_6$:

| | C % | H % | N % | O % |
|---|---|---|---|---|
| Calculated: | 68.27 | 7.66 | 3.06 | 21.01 |
| Found: | 67.76 | 7.67 | 3.06 | 21.01 |

(6) UV absorption (in MeOH)

| λ max | Molar extinct. |
|---|---|
| 261 nm | ε = 33800 |
| 271 nm | ε = 43300 |
| 282 nm | ε = 33500 |
| 386 nm | ε = 1400 |

(7) IR absorption (in CHCl$_3$)
3340, 2910, 1703, 1668, 1650 1633, 1612, 1503, 1452, 1380, 1300, 1190, 1164, 1135, 1094 1040, 1003 and 913 cm$^{-1}$ (8) $^{13}$C—NMR (in CDCl$_3$)

| | |
|---|---|
|  —C— (O) | 188.1, 182.4 |
|  —NH—C— (O) | 169.4 |
|  ⟩C= | 145.2, 139.1, 137.9 |
|  ⟩CH= | 134.1, 133.6, 133.4, 131.8, 130.9, 130.4, 128.7, 123.3, 114.2 |
|  ⟩CH—O | 78.8, 72.5, 69.2 |
| OCH$_3$ | 56.6 |
| CO—CH$_2$— | 44.6 |
| CH | 40.7 |
| CH$_2$ | 36.5, 29.5, 26.6 |
|  =⟨CH$_3$ | 20.3 |
| CH$_3$ | 10.5 |

Figure 3:
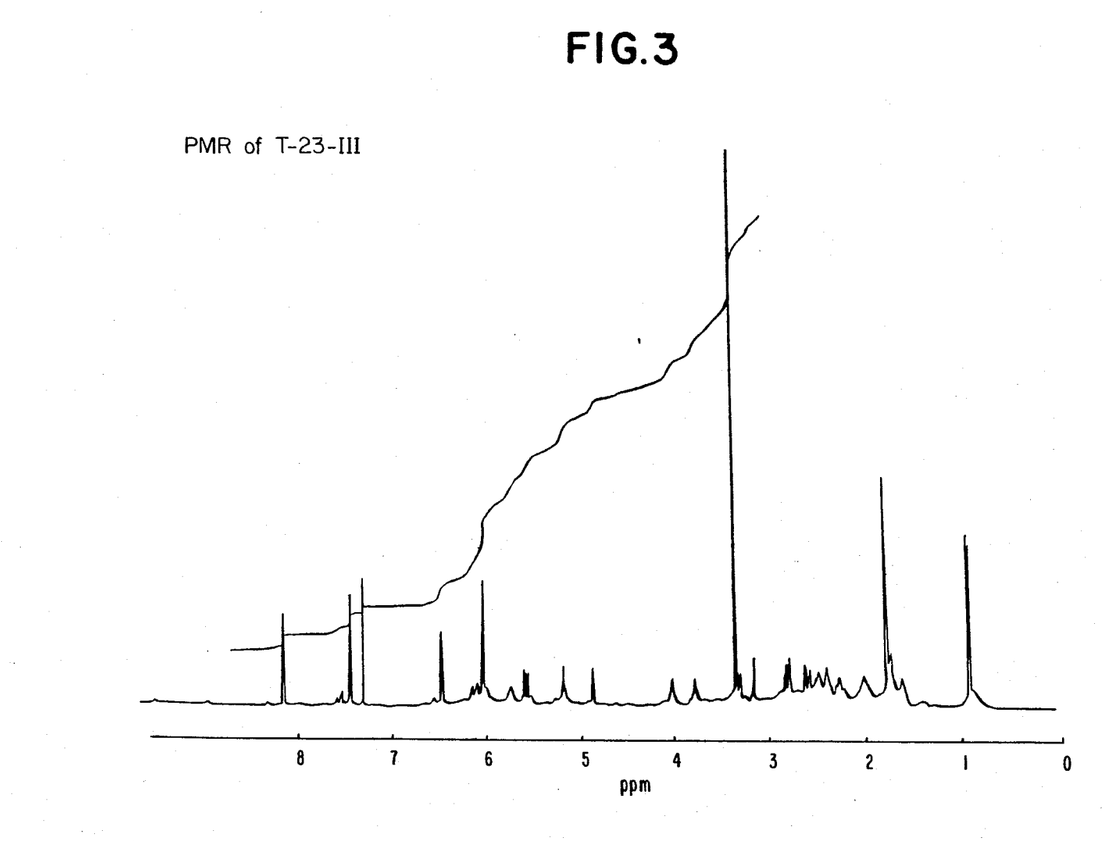

(9) PMR
See FIG. 3 as attached.
(10) Solubility in solvents:
Soluble in chloroform, ethyl acetate, methanol, ethanol, acetone, acetonitrile, benzene and toluene,
Sparingly soluble in ethyl ether,
Insoluble in petroleum ether and water.

T-23-IV substance (1) Appearance: Grayish white-colored amorphous powder
(2) Structural formula (M.W. 457)

-continued

IV

[Chemical structure IV showing a macrocyclic compound with OCH3, OH, HO, and NH groups with benzene ring bearing OH]

(3) $[\alpha]_D^{25} = +273°$ (c = 1% in MeOH)
(4) m.p. 130–132° C.
(5) Elementary analysis as $C_{36}H_{35}NO_6$:

| | C % | H % | N % | O % |
|---|---|---|---|---|
| Calculated: | 68.27 | 7.66 | 3.06 | 21.01 |
| Found: | 67.76 | 7.67 | 3.07 | 21.50 |

(6) UV absorption (in MeOH)

| λ max | Molar extinct. |
|---|---|
| 263 nm | $\epsilon = 30800$ |
| 273 nm | $\epsilon = 39800$ |
| 282 nm | $\epsilon = 30600$ |
| 307 nm | $\epsilon = 3300$ |

(7) IR absorption (KBr disc)
3340, 2920, 1645, 1540, 1462, 1378, 1300, 1224, 1195, 1145, 1090, 1000 and 854 cm$^{-1}$ (8) $^{13}$C—NMR (in d-pyridine)

| | |
|---|---|
| NH—C(=O)— | 170.3 |
| \C= / | 151.3, 141.7, 139.8, 132.9, 127.7 |
| \CH= / | 135.8, 134.8, 133.8, 131.1, 130.5, 129.8, 123.8, 116.4, 108.1 |
| CH—O | 80.8, 70.5, 68.1 |
| OCH$_3$ | 56.1 |
| CO—$\underline{C}$H$_2$— | 43.1 |
| CH | 38.9 |
| CH$_2$ | 36.2, 32.3, 25.9 |
| =/ CH$_3$ | 21.1, 9.8 |

Figure 4:
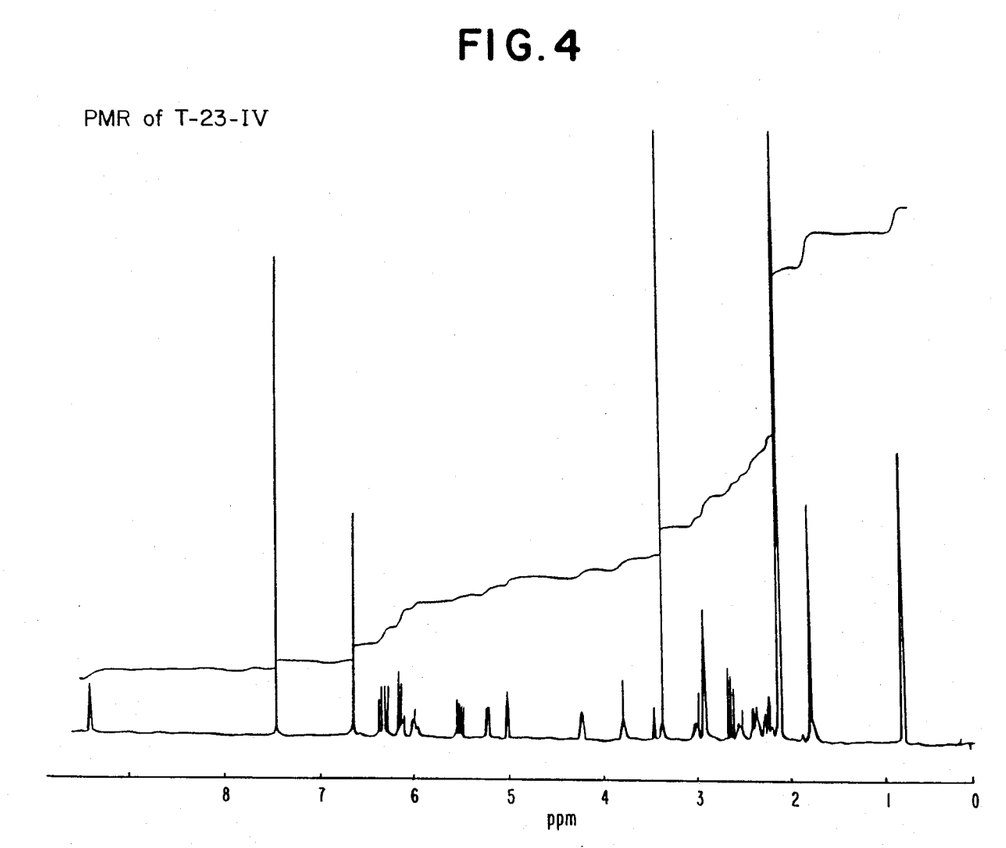

(9) PMR
See FIG. 4 as attached.
(10) Solubility in solvents:
Soluble in chloroform, ethyl acetate, methanol, ethanol, acetone and acetonitrile,
Sparingly soluble in benzene and toluene,
Insoluble in petroleum ether and water.

The T-23-I, -II, -III and -IV substances are expected to be new and useful as anti-tumor agents because they have some significant effect to inhibit the growth of several types of tumor cells. Further, the T-23-III and -IV substances are useful as intermediates to produce any new compounds by introducing a various substituent into the 11-hydroxyl group of said T-23-III or -IV substance.

The physiological properties of each of the T-23-I, -II, -III and -IV substances are shown below:

T-23-I substance (1) Antimicrobial activity against yeasts and fungi

TABLE 1

| Test microorganism | MIC (μg/ml) |
|---|---|
| *Aspergillus japonicus* | 12.5 |

TABLE 1-continued

| Test microorganism | MIC (μg/ml) |
|---|---|
| (IAM 2016) | |
| *Mucor pusillus* (IAM 6122) | 12.5 |
| *Penicillium chrysogenum* (IAM 7106) | 8.0 |
| *Saccharomyces cerevisiae* (IFO 0304) | 4.0 |
| *Saccharomyces rouxii* (IFO 0505) | 4.0 |
| *Candida utilis* (IFO 0396) | 4.0 |

The MIC (minimum inhibitory concentration) value of the T-23-I substance was determined by cultivation of a microorganism in a medium containing 1.0% glucose and 0.2% malt extract at 30° C. for 72 hours by a dilution method.

(2) Anti-tumor activity (in vitro) against L-5178Y lymphoma cells

TABLE 2

| Conc. (μg/ml) | State of cell growth |
|---|---|
| 4.0 | − |
| 2.0 | − |
| 1.0 | − |
| 0.5 | − |
| 0.25 | ± |
| 0.125 | + |

The cell growth was observed by a dilution method using an Eagle-NEM medium (Nissui) supplemented with 10% horse serum and 100 mg/l asparagine and cultivated at 37° C. for 120 hours. The T-23-I substance in ethanol solution was added to an assay system.

(3) Anti-tumor activity against mouse leukemia P-388

TABLE 3

| Dosage | Increased life span T/C (%) |
|---|---|
| 24 mg/kg/day × 2 times | 56.0 |
| 12 mg/kg/day × 2 times | 123.3 |
| 6 mg/kg/day × 2 times | 120.2 |
| 3 mg/kg/day × 2 times | 105.7 |
| 1.5 mg/kg/day × 2 times | 107.3 |
| 0.75 mg/kg/day × 2 times | 105.7 |
| 0 mg/kg/day × 2 times | 100 |

To six CDF$_1$ male mice (20±1 g) of one group, $10^6$ ascites tumor P-388 cells were transplanted intraperitoneally. The test material was administered first 24 hours and then 120 hours after transplantation. The dose of the test material suspended in gum arabic was 0.2 ml for each time. Increased life span was expressed in terms of % of the life span of the control group (administered with a gum arabic suspension).

(4) Acute toxicity:
LD$_{50}$ (mice, ip): 55.9 mg/kg

T-23-II substance (1) Antimicrobial activity against yeasts and fungi

TABLE 4

| Test microorganism | MIC (μg/ml) |
|---|---|
| *Aspergillum japonicus* (IAM 2016) | 12.5 |
| *Mucor pusillus* (IAM 6122) | 12.5 |
| *Penicillium chrysogenum* | 12.5 |

TABLE 4-continued

| Test microorganism | MIC (μg/ml) |
| --- | --- |
| (IAM 7106) | |
| Saccharomyces cerevisiae (IFO 0304) | 4.0 |
| Saccharomyces rouxii (IFO 0505) | 4.0 |
| Candida utilis (IFO 0396) | 4.0 |

The MIC (minimum inhibitory concentration) value of the T-23-II substance was determined by cultivation of a microorganism in a medium containing 1.0% glucose and 0.2% malt extract at 30° C. for 72 hours by a dilution method.

(2) Anti-tumor activity (in vitro) against L-5178Y lymphoma cells

TABLE 5

| Conc. (μg/ml) | State of cell growth |
| --- | --- |
| 4.0 | − |
| 2.0 | − |
| 1.0 | − |
| 0.5 | − |
| 0.25 | − |
| 0.125 | + |

The cell growth was observed by a dilution method using an Eagle-NEM medium (Nissui) supplemented with 10% horse serum and 100 mg/l asparagine and cultivated at 37° C. for 120 hours. The T-23-II substance in ethanol solution was added to an assay system.

(3) Anti-tumor activity against mouse sarcoma 180

TABLE 6

| Dosage | Increased life span T/C (%) |
| --- | --- |
| 20 mg/kg/day × 4 times | 138.7 |
| 6.6 mg/kg/day × 4 times | 115.0 |
| 2.2 mg/kg/day × 4 times | 95.6 |
| 0.7 mg/kg/day × 4 times | 109.6 |
| 0 mg/kg/day × 4 times | 100 |

To six ICR male mice (25±1 g) of one group, $10^6$ sarcoma 180 ascites tumor cells were transplanted intraperitoneally. The test material was administered first three hours after transplantation and then four times every 24 hours. The dose of the test material (T-23-II substance) suspended in gum arabic was 0.2 ml for each time. Increased life span was expressed in terms of % of the life span of the control group (administered with a gum arabic suspension).

(4) Anti-tumor activity against mouse leukemia P-388

TABLE 7

| Dosage | Increased life span T/C (%) |
| --- | --- |
| 20 mg/kg/day × 6 times | 135.7 |
| 10 mg/kg/day × 6 times | 120.2 |
| 5 mg/kg/day × 6 times | 127.1 |
| 2.5 mg/kg/day × 6 times | 109.9 |
| 1.25 mg/kg/day × 6 times | 130.0 |
| 0 mg/kg/day × 6 times | 100.0 |

To six $CDF_1$ male mice (20±1 g) of one group, $10^6$ ascites tumor P-388 cells were transplanted intraperitoneally. The test material was administered first 24 hours after transplantation of then six times every 24 hours. The dose of the test material suspended in gum arabic was 0.2 ml for each time. Increased life span was expressed in terms of % of the life span of the control group (administered with a gum arabic suspension).

(5) Acute toxicity
$LD_{50}$ (mice, ip): 85.5 mg/kg

T-23-III substance (1) Anti-tumor activity against P-388 ascites tumor cell

The cell growth of the P-388 ascites tumor cells maintained in the abdominal cavity of $CDF_1$ mice was observed by a dilution method using the cultivation in a series of the RPMI-1640 media supplemented with 10% bovine calf serum and 10 μM 2-hydroxyethyl disulfide for 96 hours. The cell growth inhibition observed is as follows:

TABLE 8

| Conc. (μg/ml) | Cell growth inhibition |
| --- | --- |
| 20 | + |
| 10 | + |
| 5 | + |
| 2.5 | + |
| 1.25 | ± |
| 0.6 | − |
| 0.3 | − |
| 0.15 | − |

(2) Acute toxicity
$LD_{50}$ (mice, ip): Ca. 250 mg/kg

T-23-IV substance (1) Anti-tumor activity against P-388 ascites tumor cell

The cell growth of the P-388 ascites tumor cells maintained in the abdominal cavity of $CDF_1$ mice was observed by a dilution method using the cultivation in a series of the RPMI-1640 media supplemented with 10% bovine calf serum and 10 μM 2-hydroxyethyl disulfide for 96 hours. The cell growth inhibition observed is as follows:

TABLE 9

| Conc. (μg/ml) | Cell growth inhibition |
| --- | --- |
| 20 | + |
| 10 | + |
| 5 | + |
| 2.5 | + |
| 1.25 | + |
| 0.6 | ± |
| 0.3 | − |
| 0.15 | − |

(2) Acute toxicity
$LD_{50}$ (mice, ip): Ca. 280 mg/kg

An additional feature of the present invention is to use any one of the T-23-I, -II, -III and -IV substances of the invention in the form of therapeutic agents or formulations which contain one of the said substances as the active ingredient together with conventional carriers and diluents. The therapeutic agents or formulations are prepared in a conventional manner by compounding an appropriate dose with the conventional liquid carriers and the conventional pharmaceutical auxiliaries for the desired parental administration. Suitable carriers may be physiological saline and physiologically compatible polyethylene glycols, and suitable auxiliaries may include Tween-80, etc., so as to form a solution or suspension. Individual doses of the active substance may be considered as 1–50 mg/kg and preferably 2–15 mg/kg daily.

The following are the non-limitative examples to illustrate the present invention.

EXAMPLE 1

The strain of Streptomyces T-23 was stored as a slope containing 1.0% soluble starch, 0.2% yeast extract and 1.5% agar. The spores of the organism from well grown agar slant were aseptically inoculated into an inoculum culture medium (containing 1.0% soluble starch, 1.0% molasses, 1.0% meat extract and 1.0% polypeptone (adjusted to pH 7.0) in a 500 ml Ehlenmyer flask. The flask was incubated on a rotary shaker at 30° C. for 48 hours. The resulting cultured seed was transferred in each 0.5 ml portions to a number of Ehlenmyer flasks each containing 100 ml of the smae culture medium as above. Cultivation was conducted with shaking at 30° C. for 24 hours thereby to obtain a seed inoculum for the production culture using a jar fermenter. For the production culture, six 30 1-capacity jar fermenters each containing 15.0 l of a medium (pH 7.0) containing 1.0% glucose, 1.5% soluble starch, 1.5% soya flour, 0.2% dried yeast, 0.2% ammonium sulfate, 0.5% sodium chloride, 0.4% precipitated calcium carbonate and 0.33% antifoaming agent (Toshiba "Silicone" YMA 6509) was used. The inoculum obtained was added to each fermenters, and cultivation with aeration and agitation (15.0 l/min., 200 r.p.m.) was carried out at 30° C. for 24 hours.

After completion of the cultivation, the culture broth was adjusted to pH 5.8 with 4.0N sulfuric acid. The mycelium was recovered by means of a centrifugal machine, soaked in 20 ml of 60% aqueous acetone with stirring for a short while and then allowed to stand. Then, the total mixture was filtered to remove the undissolved residue and the supernatant (extract) was recovered. The same procedure was repeated twice. The extracts combined amounted up to 40 ml. From this, acetone was evaporated under reduced pressure thereby to leave 18.0 l of an aqueous solution. To this solution (18.0 l), 6.5 kg sodium chrolide was added, and the resulting solution was extracted twice with each 9.0 l ethyl acetate. The ethyl acetate solution obtained was added with 1.0% $Na_2SO_4$ and then kept still. After dehydration, the solution was concentrated to a small volume under reduced pressure. To the concentrated liquid, an adequate volume of hexane was added, thereby to have a crude precipitate containing T-23-I and -II substances. The precipitate thus obtained was washed with hexane and then dried in vacuo to yield 42 g of crude mixture of T-23-I and -II substances. The crude powder thus obtained was dissolved in 100 ml of chloroform and the resulting solution was subjected to a silicic acid column chromatography (packed with 400 g of silica gel). Elution with benzene followed by a mixture of benzene/acetone (4:1) was carried out thereby to effect the fractionation of the T-23-I substance from impurities. By further use of benzene/acetone (7:3), T-23-II substance was successively eluated. The portions each containing T-23-I and -II substances were individually concentrated under reduced pressure. These concentrated portions were individually added with an adequate volume of hexane. The crystalline solid of T-23-I substance obtained was 1.5 g and that of T-23-II substance was 11.7 g.

EXAMPLE 2

Cultivation of Streptmyces T-23 strain was carried out as in Example 1. The resulting culture broth was centrifuged to obtain a supernatant. 10.0 l of this supernatant was passed through a column packed with a non-ionic exchange resin HP-20, and the column was washed with water. The fractions containing T-23-I and -II substances were eluted with 2.0 l of 50% aqueous acetone. Acetone was evaporated in vacuo to obtain an aqueous solution, which was then extracted twice with ethyl acetate. The extract thus obtained was added with anhydrous $Na_2SO_4$ and kept still for a while. The extract was concentrated in vacuo to yield 2.0 g of a dark brown oil. The oil thus obtained was dissolved in 10 ml of chloroform. The solution was subjected to a silicic acid column chromatography. Elution with benzene followed by a mixture of benzene/acetone (4:1) was effective for the isolation and purification of T-23-I substance. By further elution with benzene/acetone (7:3), T-23-II substance was obtained. The fractions each containing T-23-I and -II substances were individually concentrated in vacuo. These concentrates were individually added with hexane to form precipitates. The precipitates were individually collected, washed with hexane and then dried in vacuo. Crude T-23-I substance obtained was 48 mg and crude T-23-II substance 0.63 g.

EXAMPLE 3

To 100 ml of methanol having 0.1 g of ferric chloride dissolved therein, 1.25 g of T-23-II substance was dissolved with stirring under ice-cooling, and then the resulting solution was allowed to stand for 15 minutes, followed by concentration in vacuo. The reaction mixture thus obtained was added with 100 ml of ethyl acetate to form a solution, which was filtered through a glass filter. From the filtrate ethyl acetate was removed again by evaporation in vacuo thereby to yield 1.05 g of T-23-I substance as yellow powder.

EXAMPLE 4

700 mg of T-23-II substance was dissolved in 70 ml of dry tetrahydrofuran to produce a solution which was cooled to $-15°$ C. To the solution with stirring, 150 mg of lithium aluminum hydride ($LiAlH_4$) was added in three portions to effect a reaction. 200 ml of ethyl acetate was added dropwise, and further 100 ml of 0.1M phosphate buffer solution (pH 6.8) added. The solvent layer was separated from the aqueous layer and then dried with anhydrous sodium sulfate. The resulting dried solution was concentrated, and the resulted concentrate was then treated by thin layer chromatography using a silicic acid plate (Merck Art. 5717) and a benzene/ethylacetate (2:3) solvent. After the development, the yellow band portions were collected and elution was conducted with ethylacetate/methanol. The eluate was dried in vacuo to yield 260 mg of T-23-III substance. Yield 52%.

EXAMPLE 5

700 mg of T-23-II substance was dissolved in 70 ml of dry tetrahydrofuran to produce a solution which was cooled to $-15°$ C. To the solution with stirring, 150 mg of lithium aluminum hydrate ($LiAlH_4$) was added in three portions to effect a reaction. 200 ml of ethyl acetate was added dropwise, and further 100 ml of 0.1M phosphate buffer solution (pH 6.8) added. The solvent layer was separated from the aqueous layer and then dried with anhydrous sodium sulfate. The resulting dry solution was concentrated. The concentrate obtained was then treated by thin layer chromatography using a silicic acid plate (Merck Art. 5717) and a benzene/ethylacetate (2:3) solvent. After the development, the bands emitting blue fluorescence under a UV lamp were collected, and elution was conducted with ethylacetate/methanol. The eluate was made solvent-free. 65 mg of T-23-IV substance was obtained. Yield 13%.

EXAMPLE 6

700 mg of T-23-II substance was dissolved in 70 ml of dry tetrahydrofuran to produce a solution which was cooled to −15° C. To the solution with stirring, 150 mg of lithium aluminum hydride (LiAlH₄) was added in three portions to effect a reaction. 200 ml of ethyl acetate was added dropwise, and 100 ml of 0.1M phosphate buffer solution (pH 6.8) also added. The solvent layer was separated and then dried with anhydrous sodium sulfate. The resulted dry solution was concentrated. The concentrate obtained was then treated by thin layer chromatography using a silicic acid plate (Merck Art. 5717) and a benzene/ethylacetate (2:3) solvent. After the development, the yellow-colored bands on the plate and the bands emitting blue fluorescence under a UV lamp were individually collected. They were eluted individually with ethylacetate/methanol. The solvent was removed from the individual eluates, thereby to obtain 260 mg (52%) of T-23-III substance from the yellow band fraction and 65 mg (13%) of T-23-IV substance from the blue fluorescence band fraction.

What we claim is:

1. A compound of the formula or wherein R is hydrogen or a group

2. A compound as claimed in claim 1, wherein R is hydrogen.

3. A compound as claimed in claim 1, wherein R is

4. A compound as claimed in claim 3, wherein said R is in the D-form.

* * * * *

UNITED STATES PATENT AND TRADEMARK OFFICE
CERTIFICATE OF CORRECTION

PATENT NO. : 4,521,339                             Page 1 of 3
DATED      : June 4, 1985
INVENTOR(S): Otake, et al.

It is certified that error appears in the above-identified patent and that said Letters Patent is hereby corrected as shown below:

Column 1, line 55: amend "oxydation" to read --oxidation--.

Column 13, line 66: amend "Streptmyces" to read --Streptomyces--.

Claim 1, column 16: amend first formula to read:

UNITED STATES PATENT AND TRADEMARK OFFICE
CERTIFICATE OF CORRECTION

PATENT NO. : 4,521,339

DATED : June 4, 1985

INVENTOR(S) : Otake, et al.

It is certified that error appears in the above-identified patent and that said Letters Patent is hereby corrected as shown below:

Claim 1, column 16: amend second formula to read:

UNITED STATES PATENT AND TRADEMARK OFFICE
CERTIFICATE OF CORRECTION

PATENT NO. : 4,521,339

DATED : June 4, 1985

INVENTOR(S) : Otake, et al.

It is certified that error appears in the above-identified patent and that said Letters Patent is hereby corrected as shown below:

Claim 1, column 16 (third formula) and formula in Claim 3, column 16; amend each to read:

Signed and Sealed this

Twenty-ninth Day of July 1986

[SEAL]

Attest:

DONALD J. QUIGG

Attesting Officer

Commissioner of Patents and Trademarks